United States Patent
Stevens (10) Patent No.: US 10,386,333 B2
(45) Date of Patent: Aug. 20, 2019

(54) PERFORMING CHEMICAL REACTIONS AND/OR IONIZATION DURING GAS CHROMATOGRAPHY-MASS SPECTROMETRY RUNS

(71) Applicant: Waters Technologies Corporation, Milford, MA (US)

(72) Inventor: Douglas M. Stevens, Holden, MA (US)

(73) Assignee: WATERS TECHNOLOGY CORPORATION, Milford, MA (US)

( * ) Notice: Subject to any disclaimer, the term of this patent is extended or adjusted under 35 U.S.C. 154(b) by 74 days.

(21) Appl. No.: 14/376,862

(22) PCT Filed: Jan. 30, 2013

(86) PCT No.: PCT/US2013/023765
§ 371 (c)(1),
(2) Date: Aug. 6, 2014

(87) PCT Pub. No.: WO2013/119435
PCT Pub. Date: Aug. 15, 2013

(65) Prior Publication Data
US 2015/0024510 A1    Jan. 22, 2015

Related U.S. Application Data

(60) Provisional application No. 61/597,212, filed on Feb. 10, 2012.

(51) Int. Cl.
*G01N 27/62*        (2006.01)
*G01N 30/72*        (2006.01)

(52) U.S. Cl.
CPC ......... *G01N 27/62* (2013.01); *G01N 30/7206* (2013.01); *Y10T 436/24* (2015.01)

(58) Field of Classification Search
CPC ............. Y10T 436/24; Y10T 436/212; G01N 30/7266; G01N 30/72; G01N 33/58;
(Continued)

(56) References Cited

U.S. PATENT DOCUMENTS 6,469,297 B1   10/2002   Kato
7,375,316 B2    5/2008   Yamada et al.
(Continued)

FOREIGN PATENT DOCUMENTS

EP        0266334        4/1988

OTHER PUBLICATIONS

Hunt et al., "Studies of Negative Ions by Collision-Induced Decomposition and Hydrogen-Deuterium Exchange Techniques", Environmental Health Perspectives, 1980, v. 36, pp. 33-38.*
(Continued)

*Primary Examiner* — Xiaoyun R Xu (57) ABSTRACT

A gas chromatography-mass spectrometry (GC-MS) method that includes performing a first GC-MS run on a sample using a gas chromatography-mass spectrometry system. Performing the first GC-MS nm includes i) passing a first flow of a carrier gas carrying a first portion of the sample through a gas chromatograph to provide a first effluent; ii) generating first ions under protonation conditions by passing the first effluent through an atmospheric pressure ionization source; iii) passing the first ions through a mass spectrometer; and iv) recording first GC-MS data for the first ions. The method also include performing a second GC-MS run on the sample using the gas chromatography-mass spectrometry system.

11 Claims, 3 Drawing Sheets

(58) Field of Classification Search
CPC ............ G01N 27/622; G01N 1/2202; G01N 2030/027; G01N 24/084; G01N 30/7206; H01J 49/00; H01J 49/0431; H01J 49/004; H01J 49/0027
See application file for complete search history.

(56) References Cited

U.S. PATENT DOCUMENTS

| | | | |
|---|---|---|---|
| 7,642,510 | B2 | 1/2010 | McEwen |
| 2002/0086434 | A1* | 7/2002 | Roussis ............ G01N 33/2835 436/139 |
| 2003/0124610 | A1 | 7/2003 | Kvalheim et al. |
| 2003/0175979 | A1 | 9/2003 | Lam et al. |
| 2006/0255261 | A1 | 11/2006 | Whitehouse et al. |
| 2011/0290994 | A1 | 12/2011 | Jarrell |

OTHER PUBLICATIONS

Davies et al. "Hydrogen/deuterium exchange on aromatic rings during atmospheric pressure chemical ionization mass spectrometry", Rapid. Commun. Mass Spectrom., 2010, v. 24, pp. 1105-1110.*

Ahmed and Kim, "Atmospheric Pressure Photo Ionization Hydrogen/Deuterium Exchange Mass Spectrometry—a Method to Differentiate Isomers by Mass Spectrometry", J. Am. Mass Spectrom., 2013, v. 24, pp. 1900-1905.*

Acter et al. "Optimization and Application of APCI Hydrogen-Deuterium Exchange Mass Spectrometry (HDX MS) for the Speciation of Nitrogen Compounds", J. Am. Mass Spectrom., 2015, v. 26, pp. 1522-1531.*

Wolffe and Laures, "'On-the-fly' hydrogen/deuterium exchange liquid chromatography/mass spectrometry using a dual-sprayer atmospheric pressure ionisation source", Rapid Comm. Mass Spectrom., 2006, v. 20, pp. 3769-3779.*

Stevens and Hsu, Use of atmospheric pressure gas chromatography mass spectrometry (APGC/MS) for novel applications of petroleum and chemical research, Conference Paper, Am. Chem. Soc., Div. Fuel Chem., Aug. 2011, v. 56, No. 2, pp. 419-420.*

Marotta et al.; "A Mass Spectrometry Study of Alkanes in Air Plasma at Atmospheric Pressure", J. Am. Soc. Mass spectrom 2009, 20, 697-707.

International Search Report for PCT/US2013/023765, dated Apr. 8, 2013, 5 pages.

International Written Opinion Report for PCT/US2013/023765, dated Apr. 8, 2013, 7 pages.

Wang et al; "Gas Chromatographic-Ion Trap Mass Spectrometric Analysis of Volatile Organic Compounds by Ion-Molecule Reactions Using the Electron-Deficient Reagent Ion CCI3+", J. Am. Soc. Mass Spectrom, 2011, vol. 22, pp. 1839-1850.

Hunt et al.; "Chemical Ionization Mass Spectrometry II., Differentiation of Primary, Secondary, and Tertiary Amines", Tetrahedron Letters, vol. 12, Issue 47, 1971, pp. 4539-4542.

Vaidyanathan et al.; "Explanatory Optimization of Protein Mass Spectrometry via Genetic Search", Anal. Chem. 2003, vol. 75, pp. 6679-6686.

Rand et al.; "ETD in a Traveling Wave Ion Guide at Tuned Z-Spray Ion Source Conditions Allows for Site-Specific Hydrogen/Deuterium Exchange Measurements", J. Am. Soc. Mass Spectrom, (2011), vol. 22, pp. 1784-1793.

Buchanan, Michelle V.; "Mass Spectral Characterization of Nitrogen-Containing Compounds with Ammonia Chemical Ionization", Anal. Chem, 1982, vol. 54, pp. 570-574.

* cited by examiner

FIG. 3

PERFORMING CHEMICAL REACTIONS AND/OR IONIZATION DURING GAS CHROMATOGRAPHY-MASS SPECTROMETRY RUNS

RELATED APPLICATIONS

This application is the National Stage of International Application No. PCT/US2013/023765, filed on Jan. 30, 2013, which claims priority to and benefit of U.S. Provisional Patent Application No. 61/597,212 entitled "Performing Chemical Reactions and/or Ionization During Gas Chromatography-Mass Spectrometry Runs," filed Feb. 10, 2012. The contents and teachings of each of these applications are hereby expressly incorporated herein by reference in their entirety.

TECHNICAL FIELD

This disclosure relates to performing chemical reactions and/or ionization during gas chromatography-mass spectrometry runs.

BACKGROUND

In gas chromatography-mass spectrometry (GC-MS), a flow of a mobile phase gas (or "carrier gas"), typically an inert gas, sweeps a sample through a gas chromatography (GC) column. Generally, the GC column includes a layer of polymer or liquid that acts as a stationary phase. The sample is separated into its constituent parts (i.e., separate compounds) as it passes through the column and interacts with the stationary phase material. As a result, the various compounds that make up the sample elute from the column at different times. The effluent from the column is exposed to an ionization source to ionize analyte molecules in the effluent so that ionized analyte molecules can then be detected using a mass spectrometer.

SUMMARY

This disclosure is based, in part, on the realization that an atmospheric pressure ionization source can be utilized to perform chemical reactions, as an alternative to in addition to ionization, during gas chromatography-mass (GC-MS) spectrometry runs.

One aspect provides a gas chromatography-mass spectrometry (GC-MS) method that includes performing a first GC-MS run on a sample using a gas chromatography-mass spectrometry system. Performing the first GC-MS run includes i) passing a first flow of a carrier gas carrying a first portion of the sample through a gas chromatograph to provide a first effluent; ii) generating first ions under protonation conditions by passing the first effluent through an atmospheric pressure ionization source; iii) passing the first ions through a mass spectrometer; and iv) recording first GC-MS data for the first ions. The method also include performing a second GC-MS run on the sample using the gas chromatography-mass spectrometry system. Performing the second GC-MS run includes i) passing a second flow of the carrier gas carrying a second portion of the sample through the gas chromatograph to provide a second effluent; ii) generating second ions under deuteration conditions by passing the second effluent through the atmospheric pressure ionization source; iii) passing the second ions through a mass spectrometer; and iv) recording second GC-MS data for the first ions. The method also includes comparing the first and second GC-MS data to assess the presence of one or more compounds in the sample that ionize by hydride abstraction.

Implementations of this method can include one or more of the following features.

In some implementations, the method also includes identifying one or more analyte ions that exhibit a mass shift when ionized under deuteration conditions based on the comparison.

In certain implementations, the method also includes stripping data corresponding to compounds that ionize by hydride abstraction from the second GC-MS data based on the comparison.

The method can also include switching between the protonation conditions and the deuteration conditions.

The step of switching can include replacing a first reagent inside the atmospheric pressure ionization source with a second reagent, wherein the first reagent or the second reagent is a deuterated reagent (e.g., D20, MeOH-d3, MeOH-d4, etc.).

In some implementations, the atmospheric pressure ionization source includes a source enclosure, a chamber device disposed within the source enclosure and including at least one wall defining a chamber, and a corona discharge pin disposed within the source enclosure and extending into the chamber. In such implementations, passing the first effluent through the atmospheric pressure ionization source can include passing the first effluent into the chamber and through a corona discharge provided by the corona pin, and passing the second effluent through the atmospheric pressure ionization source can include passing the second effluent into the chamber and through a corona discharge provided by the corona pin.

Another aspect features a gas chromatography-mass spectrometry (GC-MS) method that includes performing a first GC-MS run on a sample using a gas chromatography-mass spectrometry system. Performing the first GC-MS run includes i) passing a first flow of a carrier gas carrying a first portion of the sample through a gas chromatograph to provide a first effluent; ii) generating first ions under conditions that inhibit or prevent the addition of halogens to aromatic analytes by passing the first effluent through an atmospheric pressure ionization source; iii) passing the first ions through a mass spectrometer; and iv) recording first GC-MS data for the first ions. The method also includes performing a second GC-MS run on the sample using the gas chromatography-mass spectrometry system. Performing the second run includes i) passing a second flow of the carrier gas carrying a second portion of the sample through the gas chromatograph to provide a second effluent; ii) generating second ions under conditions that promote the addition of halogens to aromatic analytes by passing the second effluent through the atmospheric pressure ionization source; iii) passing the second ions through a mass spectrometer; and iv) recording second GC-MS data for the first ions. The method also includes comparing the first and second GC-MS data to assess the presence of one or more aromatic analytes in the sample.

Implementations of this method can include one or more of the following features.

In some implementations, the method also includes switching between the conditions that inhibit or prevent the addition of halogens to aromatic analytes and the conditions that promote the addition of halogens to aromatic analytes.

The switching step can include changing a flow rate of a counter-current gas and a flow rate of an auxiliary gas.

In some examples, the switching step includes reducing the counter-current gas flow rate from about 40 liters/hour to about 25 liters/hour, and reducing the flow rate of the auxiliary gas from about 400 liters/hour to about 0 liters/hour.

In certain implementations, the switching step includes increasing the counter-current gas flow rate from about 25 liters/hour to about 40 liters/hour, and increasing the flow rate of the auxiliary gas from about 0 liters/hour to about 400 liters/hour.

In some implementations, the method includes providing a chlorinated reagent within a source enclosure of the atmospheric pressure ionization source.

In certain implementations, the method includes identifying one or more analyte ions that exhibit a mass shift when ionized under the conditions that promote the addition of halogens to aromatic analytes based on the comparison.

The method can also include stripping data corresponding to compounds that do not exhibit a mass shift when ionized under the conditions that promote the addition of halogens to aromatic analytes from the second GC-MS data based on the comparison.

Another aspect provides a method that includes passing a flow of a carrier gas carrying a portion of the sample through a gas chromatograph to provide an effluent; adding a halogen to an aromatic analyte and generating ions by passing the effluent through an atmospheric pressure ionization source that includes a source of the halogen; and passing the ions through a mass spectrometer.

Implementations of this method can include or more of the following features.

In some implementations, the method includes providing a chlorinated reagent within a source enclosure of the atmospheric pressure ionization source.

The method can also include switching between conditions that inhibit or prevent the addition of halogens to aromatic analytes in the effluent and conditions that promote the addition of halogens to aromatic analytes in the effluent.

The switching step can include changing a flow rate of a counter-current gas and a flow rate of an auxiliary gas.

In some cases, the switching step includes reducing the counter-current gas flow rate from about 40 liters/hour to about 25 liters/hour, and reducing the flow rate of the auxiliary gas from about 400 liters/hour to about 0 liters/hour.

In some examples, the switching step includes increasing the counter-current gas flow rate from about 25 liters/hour to about 40 liters/hour, and increasing the flow rate of the auxiliary gas from about 0 liters/hour to about 400 liters/hour.

Yet another aspect features a method that includes passing a flow of a carrier gas carrying a portion of the sample through a gas chromatograph to provide an effluent; generating ions by passing the effluent through an atmospheric pressure ionization source that includes a source of the halogen; passing the ions through a mass spectrometer; and providing a catalyst within the atmospheric pressure ionization source thereby preventing ionization of a certain compound or a certain class of compounds in the effluent that otherwise would ionize in the absence of the catalyst.

Implementations of this method can include one or more of the following features.

In some implementations, the atmospheric pressure ionization source includes a source enclosure, a chamber device disposed within the source enclosure and comprising at least one wall defining a chamber, and a corona discharge pin disposed within the source enclosure and extending into the chamber. In such implementations, providing the catalyst within the atmospheric pressure ionization source can include providing the catalyst within the chamber.

In certain implementations, the catalyst is provided as a coating on an inner surface of the at least one wall.

In some examples, the catalyst is provided in solid form.

In some cases, the catalyst is in liquid form.

Providing the catalyst includes inserting a vial containing the liquid form catalyst into the atmospheric pressure ionization source.

A further aspect provides a method that includes passing a flow of a carrier gas carrying a portion of the sample through a gas chromatograph to provide an effluent; generating ions by passing the effluent through an atmospheric pressure ionization source that includes a source of the halogen; passing the ions through a mass spectrometer; and providing a catalyst within the atmospheric pressure ionization source thereby causing a chemical conversion of a certain compound or a certain class of compounds within the effluent to more readily ionized species.

Implementations may include one or more of the following features.

The atmospheric pressure ionization source can include a source enclosure; a chamber device disposed within the source enclosure and comprising at least one wall defining a chamber; and a corona discharge pin disposed within the source enclosure and extending into the chamber, and providing the catalyst within the atmospheric pressure ionization source can include providing the catalyst within the chamber.

In some implementations, the catalyst is provided as a coating on an inner surface of the at least one wall. Alternatively or additionally, the catalyst can be provided in solid or liquid form.2.

In some cases, proving the catalyst includes inserting a vial containing the liquid form catalyst into the atmospheric pressure ionization source.

Implementations can provide one or more of the following advantages.

Chemical reactions can be performed in real time during gas chromatography-mass spectrometry (GC-MS) runs to provide selectivity of detection or additional substructural information for structural elucidation analyses. The ability to turn these reactions on and off through changes to source conditions but without the need for changing the reagent or physical set up of the source are possible. The capability can facilitate acquiring data of various types to serve different purposes such as unknown identification or determination of the presence of a class of compounds in a sample.

In comparison with vacuum source chemical ionization paired with gas chromatography, many of the above described approaches may not be directly applicable as the atmospheric pressure ionization source can allow for effective and easy implementation. Solvents such as D2O and MeOH-d4 can cause rapid fouling or problems sustaining vacuum in vacuum chemical ionization sources.

Other aspects, features, and advantages are in the description, drawings, and claims.

BRIEF DESCRIPTION OF THE DRAWINGS

Like reference numbers indicate like elements.

DETAILED DESCRIPTION

Figure 1:
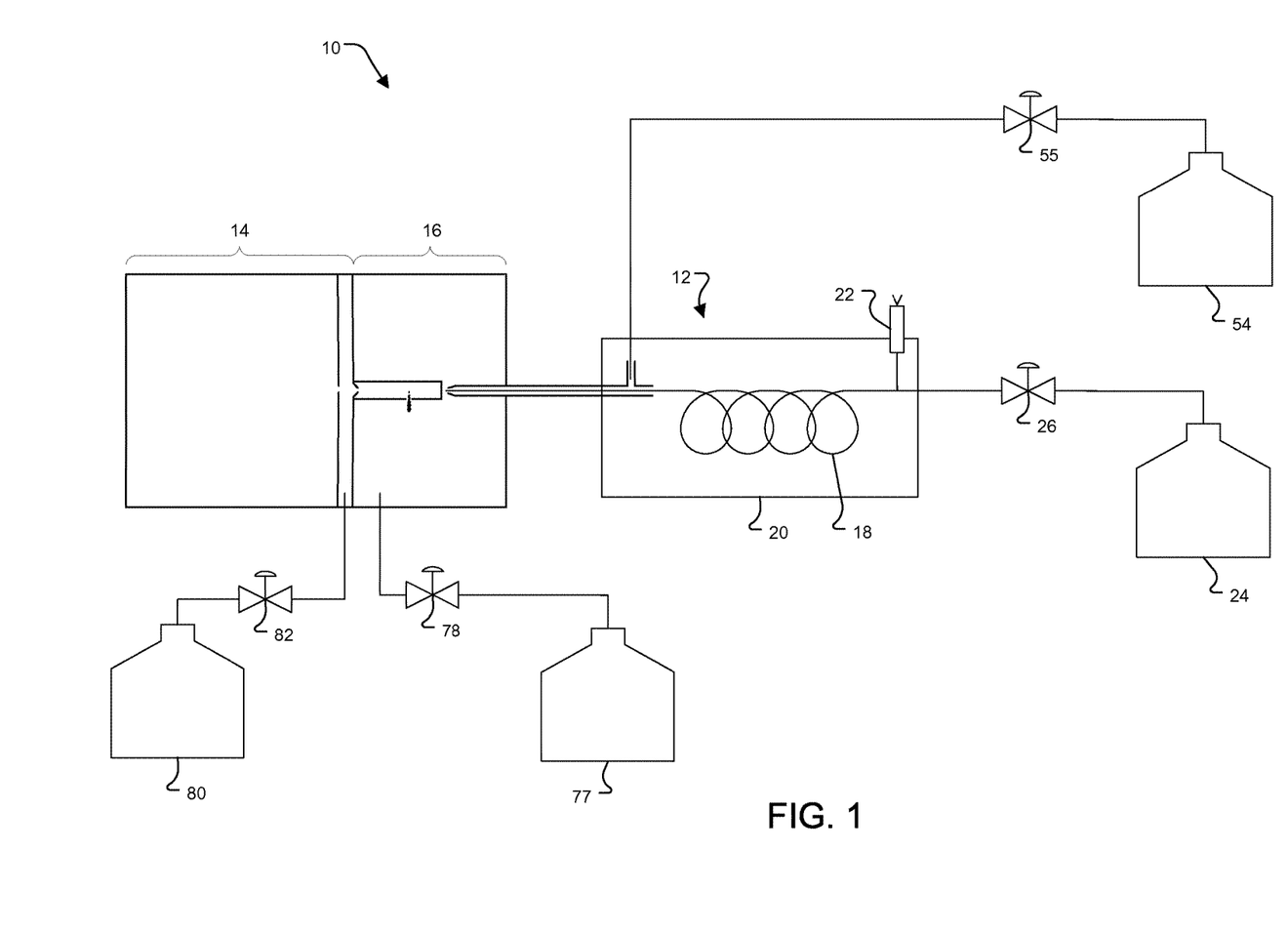
FIG. 1 is a schematic view of a gas chromatography/mass spectrometry (GC/MS) system.

Referring to FIG. 1, a gas chromatography-mass spectrometry (GC-MS) system 10 includes a gas chromatograph 12, a mass spectrometer 14, and an atmospheric pressure ionization source 16 which serves an interface between the gas chromatograph and the mass spectrometer 14 and which can be utilized as an ionization and/or chemical reaction device. A suitable atmospheric pressure ionization source is the Waters® Atmospheric Pressure Gas Chromatography (APGC) source available from Waters Corporation of Milford, Mass.

The gas chromatograph 12 includes a gas chromatography (GC) column 18 inside a temperature controlled oven 20. A sample is introduced on to the GC column 18 through a sample injector 22 into a flow of a carrier gas (e.g., helium) from a carrier reservoir 24. A carrier flow controller 26 is provided to maintain a constant flow of the carrier gas (mobile phase), which may be helium (He) gas. A flow of about 0.5 ml/minute to about 10 ml/minute (e.g., about 1 ml/minute to about 5 ml/min) would be suitable for many capillary GC columns. The GC column 18 is a coil of metal, glass, or fused silica capillary tubing, typically 0.53 mm or smaller internal diameter and 0.8 mm or smaller outside diameter, internally coated with a stationary phase suitable for effecting separation of different chemical components of the sample. The effluent from the GC column 18, including analyte molecules in a flow of the carrier gas at a pressure approximately equal to atmospheric pressure (e.g., about 980 millibars (mb) to about 1050 mb), passes into the atmospheric pressure ionization source 16.

Gas and analyte molecules emerge from the atmospheric pressure ionization source 16 and are sampled through an entrance in the mass spectrometer 14. The mass spectrometer 14 can be any mass spectrometer capable of analyzing ion present in a gas at substantially atmospheric pressure. The mass spectrometer 14 can include one or more ion traps and/or quadrupole, magnetic sector, electrostatic sector, or time-of-flight analysers. The mass spectrometer 14 can also include one or more collision cells, reaction cells or mobility separation stages for separating or fragmenting analyte ions or for reacting them with another species such as neutral molecules, ions of polarity opposite to those of the analyte ions, or electrons. Such cells can be disposed ahead of or between the analysers or traps and can include ion guides or other ion transmission devices to assist transmission of ions through the cell. The mass spectrometer 14 can also include one or more pressure reduction stages for progressively reducing the pressure, disposed between a sample cone 28 (FIG. 2) and the first of the analysers or ion traps. These pressure reduction stages can include ion guides for efficiently transmitting ions through each stage and from one stage to the next. Ion guides incorporated in the mass spectrometer can include multipole rod sets, such as quadrupoles, hexapoles, or octupoles, or ring sets or linear or quadrupole ion traps. Suitable mass spectrometers include Xevo® TQD, Xevo® TQ, Xevo® TQ-S, Xevo®G2 QTof, Xevo® Tof, Synapt® G2, Synapt® G2-S mass spectrometers all available from Waters Corporation, Milford, Mass. Selection of a mass spectrometer can be made with knowledge of the nature of the analyte molecules and the information required from the analyses.

Figure 2:
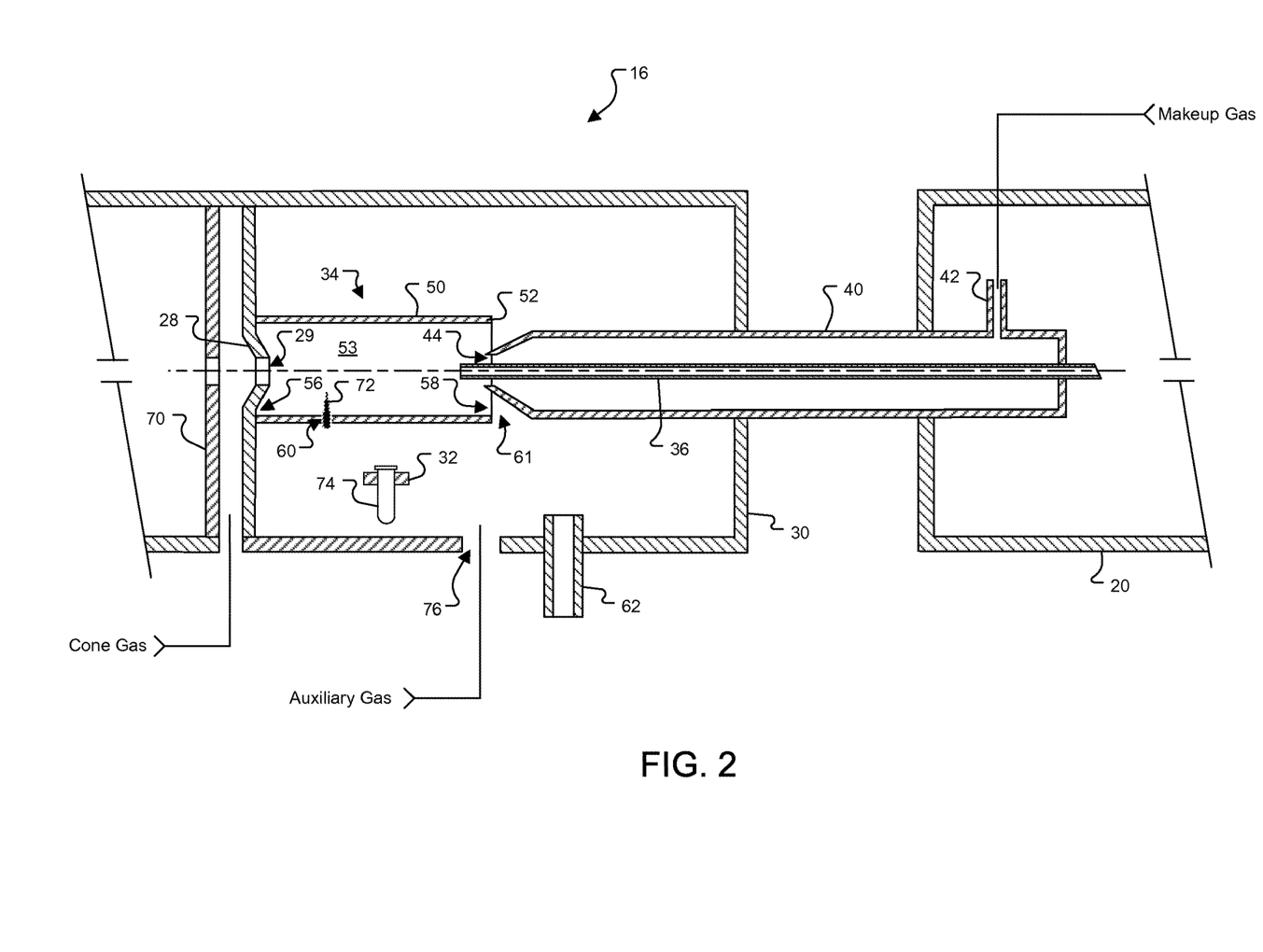
FIG. 2 is a detailed view of one arrangement of part of the system shown in FIG. 1.

Referring to FIG. 2, the atmospheric pressure ionization source 16 includes a source enclosure 30 which encloses a reagent holder 32 and a chamber device 34. An inlet tube 36 is either integral with, or is connected to, the outlet of the GC column 18 (FIG. 1). For example, the inlet tube 36 may be a distal end portion of the GC column 18. Alternatively, the inlet tube 36 may be a fused silica tube connected to the distal (outlet) end of the GC column 18. The inlet tube 36 extends through a wall of the oven 20 and then through a wall of the source enclosure 30 towards the chamber device 34.

The inlet tube 36 passes through a heated transfer line 40, which circumferentially surrounds a portion of the inlet tube 36. The transfer line 40 is capable of maintaining the temperature of the inlet tube 36 sufficiently high to prevent loss of analyte molecules as they travel through the inlet tube 36. The necessary temperature is dependent on the nature of the analyte molecules, but may typicals be in the range 100° C.-400° C.

A supply of a makeup gas (typically nitrogen or another inert gas such as argon) is provided through a transfer line inlet 42. A makeup gas flows down the transfer line 40 (at a flow rate of about 500 ml/min) and acts as a sheath gas over the inlet tube 36, supplying heat to the inlet tube 36, transfer line 40 and chamber 53 (discussed below). The makeup gas is provided from a makeup gas source 54 and can be controlled via a makeup gas flow controller 55. The makeup gas flows in the annular space between the inside of the transfer line 40 and the exterior of the inlet tube 36 and exits through a transfer line outlet 44, where it merges with the effluent from the GC column 18.

The chamber device 34 includes a housing 50 that has at least one wall 52 which defines a chamber 53. The chamber 53 has an outlet port 56, a sample port 58, and a corona pin port 60.

The housing 50 can be made from a structural material such as plastic, metal, glass, or ceramic. Suitable metals include stainless steel, titanium, aluminum, copper, brass, and other alloys. The distal (outlet) ends of inlet tube 36 and the transfer line 40 extend toward the sample port 58 such that the column effluent and the makeup gas are directed into the chamber 53. The sample port 58 is positioned with respect to the corona pin port 60 so as to allow the column effluent exiting the inlet tube 36 to be ionized. A gap 61 between the sample port 58 and the exterior of the transfer line 40 allows excess gas in the chamber 53 to vent and be carried off by a vent structure 62 of the source enclosure 30. The vent structure 62 discharges to atmospheric pressure.

The outlet port 56 is configured to be received on or about the sample cone 28 of the mass spectrometer 14. The sample cone 28 interfaces between the chamber 53 and an extraction cone 70 of the mass spectrometer 14. The sample cone 28 substantially fills the outlet port 56 to form a substantially closed end of the chamber 53. The chamber 53 has a volume of 0.5 cc to 5.0 cc when the outlet port 56 is received on the or about the sample cone 28. The addition of the chamber 53 can provide improved sensitivity. The addition of the chamber 53 can also significantly improve control of ionization and/or gas phase chemical reactions.

The chamber device 34 can be releasably affixed by a close fit of the wall 52 and the sample cone 28. Alternatively, the chamber device 34 can be affixed on or about sample cone 28 by means such as screws, cooperating threads, pins, clips, clamps, adhesives, etc.

The corona pin port 60 is constructed and arranged for receiving a corona discharge pin 72 for discharging electrons. The discharged electrons can place a charge on reagent gas molecules which in turn ionize analyte molecules in the effluent from the GC column 18. The analyte molecules are received in an opening 29 of the sample cone 28 for mass analysis.

The reagent holder 32 is disposed within the source enclosure 30 in a region outside of the chamber 53. The reagent holder 32 is configured to receive a vial 74 containing a reagent. The reagent holder 32 is positioned in a region of the source enclosure that is at a temperature sufficient to volatilize the reagent so that the reagent goes into the gas phase and is drawn into the chamber 53.

The source enclosure 30 includes an auxiliary gas port 76 for the introduction of an auxiliary gas into the source enclosure 30 in a region outside of the chamber 53. The auxiliary gas is an inert gas (e.g., nitrogen) and is provided from an auxiliary gas source 77 (FIG. 1). The flow of auxiliary gas is generally maintained at a flow rate of about 100 liters/hour to about 300 liters/hour, which can be controlled via an auxiliary gas flow controller 78 (FIG. 1). The gap 61 between the sample port 58 and the exterior of the transfer line 40 allows the gas phase reagent and auxiliary gas within the source enclosure 30 to be drawn into the chamber 53.

A counter-current (cone) gas is introduced into the mass spectrometer 14 from a counter-current gas source 80 (FIG. 1). The counter-current gas enters the chamber 53 through the opening 29 of the sample cone 28 and serves primarily to keep neutral species out of the mass spectrometer 14. The flow rate of the counter-current gas can be controlled by a counter-current gas controller 82 (FIG. 1). The flow of the counter-current gas is generally maintained at a flow rate of about 0 liters/hour to about 50 liters/hour. The counter-current gas together with the makeup gas, supplies gas (e.g., nitrogen) for plasma as well as sweeping out the chamber 53 on a chromatographic timescale.

In some cases, the makeup gas, the auxiliary gas, and the counter-current gas, or some combination thereof, may be provided from a single gas source.

The atmospheric pressure ionization source 16 can be used to ionize analyte molecules by deuteration at atmospheric pressure. Deuteration can allow certain classes of analytes such as alkanes or non-aromatic hydrocarbons to be selectively determined due to their propensity to ionize through hydride abstraction rather than through protonation. Compounds amenable to ionization via protonation will exhibit a characteristic mass shift when analyzed under deuteration conditions.

A first GC-MS run can be conducted on the GC-MS system 10 in which effluent from the GC column 18 is exposed to protonation conditions (Table 1, below) at atmospheric pressure within the atmospheric pressure ionization source 16.

TABLE 1

| | |
|---|---|
| Corona Pin Current | 0.1 to 5.0 uA |
| Sample Cone Voltage | about 10 to about 50 volts |
| Extraction Cone Voltage | about 3 volts to about 6 volts |
| Carrier Gas Flow Rate | about 0.5 ml/.min to about 10 ml. min |
| Makeup Gas Flow Rate | about 250 to about 500 ml/min |
| Auxiliary Gas Flow Rate | about 100 to about 300 liters/hour |
| Counter-Current (Cone) Gas Flow Rate | about 0 liters/hour to about 50 liters/hour |

Under protonation conditions, a vial containing a first reagent (e.g., H2O, MeOH-d0) capable of promoting protonation is placed within the reagent holder 32 inside of the source enclosure.

A second GC-MS run can be conducted in which the effluent from the GC column 18 is exposed to deuteration conditions at atmospheric pressure within the atmospheric pressure ionization source 16. The deuteration conditions are substantially the same as the protonation conditions with the exception being that the vial containing the first reagent is replaced with a vial containing a second, deuterated reagent (e.g., D2O, MeOH-d4).

The protonation and deuteration runs can be performed in either order. Data from the two runs can then be compared. Compounds amenable to protonation will exhibit a characteristic mass shift when analyzed under deuteration conditions while those that ionize by hydride abstraction (e.g., alkanes) will not exhibit a mass shift when comparing the protonation and deuteration data.

This characteristic lack of mass shift can be used to remove the data corresponding to the compounds that ionize by hydride abstraction, or, alternatively, to keep the data corresponding to the compounds that ionize by hydride abstraction (e.g., alkane data) and remove data corresponding to the compounds that ionize by protonation. In this regard, the collected data can be post-processed using a Strip function implemented in software (e.g., MassLynx™ Mass Spectrometry Software, available from Waters Corporation) to strip out the unwanted data. Such post processing can be beneficial for removing data corresponding basic components of a matrix, such as alkanes, in order to focus on trace level unknowns. Alternatively or additionally, where there is an interest in determining the relative abundance of alkanes in a matrix, such post-processing can allow for data corresponding to compounds that ionize by protonation to be removed (e.g., removed from the data of the deuteration run) in order to focus on the alkanes.

Figure 3:
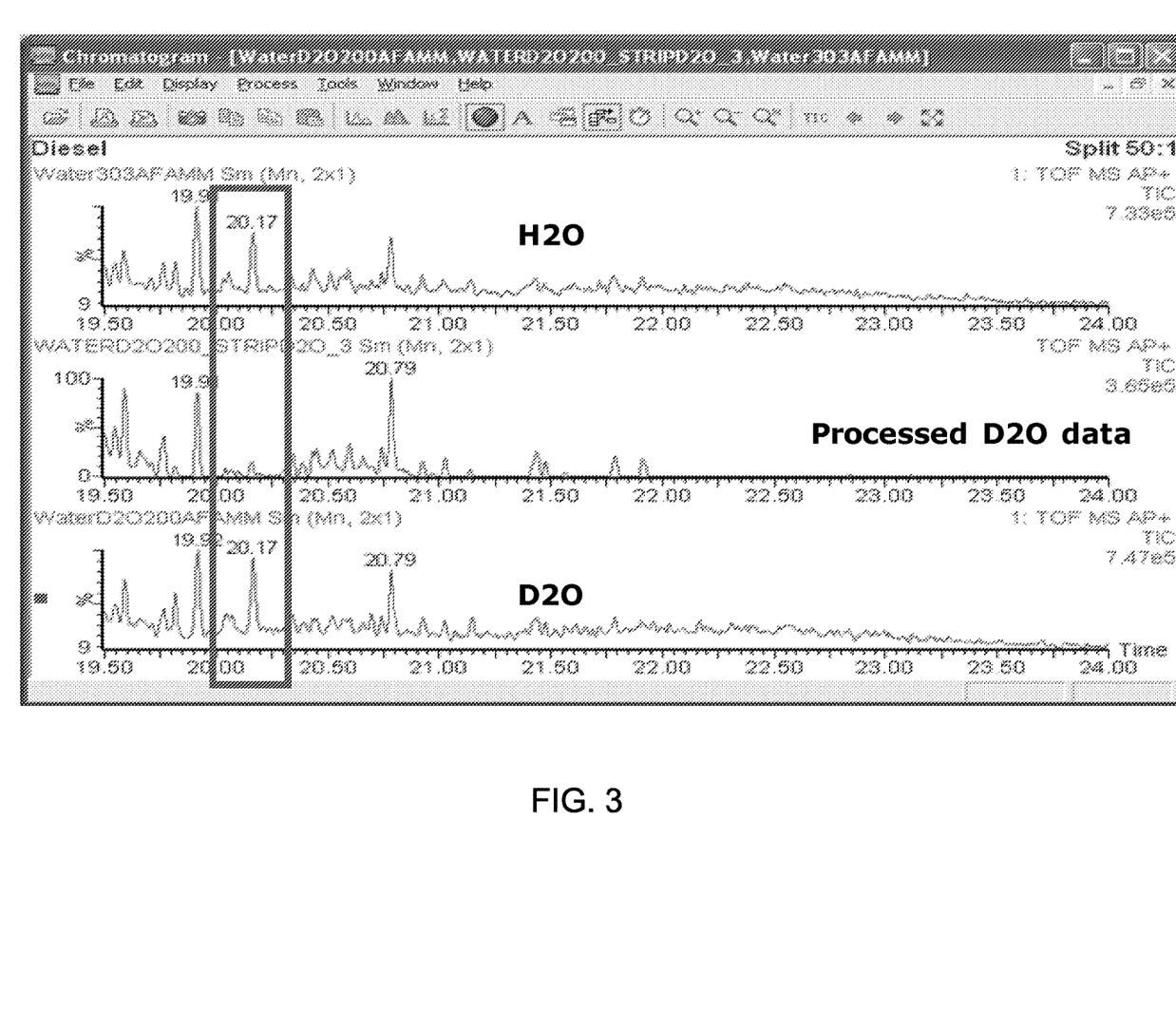
FIG. 3 illustrates a comparison of data obtained from a GC-MS run performed under protonation condition to that obtained under deuteration conditions.

FIG. 3 demonstrates one example of an approach to determining the difference between protonated unknowns versus those formed by hydride abstraction. In this example, a first run was performed on a GC-MS system, such as described above with reference to FIGS. 1 & 2, in which a sample (diesel) was injected into a flow of helium carrier gas which was passed through the gas chromatograph. The effluent from the GC column was analyzed using protonation conditions (Table 1) within the atmospheric pressure ionization source 16 with H2O as the reagent.

A second run was then performed under substantially the same conditions except that the H2O reagent in the atmospheric pressure ionization source 16 was replaced with the deuterated reagent D2O. Referring to FIG. 3, the upper trace shows the results of the first run using the protonation conditions (using H2O as the reagent), and the lower trace shows the results of the second run using the deuteration conditions (using D2O as the reagent). The data was post processed to highlight analytes that has taken on a [M+D]+ form during ionization. The peaks in the highlighted range are well differentiated from the background in the center trace because of the post processing. A Strip function was used to filter the data to show only peaks where the distinctive mass difference of 1.0063 was present in the spectrum due to the presence of [M+H]+ and [M+D]+.

FIG. 3 shows a peak at 20.17 minutes that did not form any appreciable [M+D]+. This can help to make determinations of structural differences. Close inspection of the spectra from this peak indicates the coelution of a major component that does not form [M+D]+ along with a minor component that does. One possible explanation for this is that the major component ionizes by hydride abstraction which will lead to it not taking on D during ionization, while the minor component is amendable to protonation (or in this case deuteration). So, in this example, the processed D2O data has alkanes and any other analytes that ionize through hydride abstraction depleted from the data using a post-acquisition process. As an alternative, the data could have the protonating species depleted from the run in order to highlight the compounds that ionize through hydride abstraction rather than remove them from the data.

Deuteration can also be utilized for spectral qualitative content analysis for the identification of a single compound. As previously mentioned, under protonation there is no mass shift for alkanes. If there is only protonation data, there is no way to know whether a compound is an alkane or has a double bond somewhere (an alkene). In the analysis of an unknown, it will not be clear from protonation data alone whether an ion is an alkane ion having the form [M−H]+ or an alkene ion having the form [M+H]+. Thus, an analyst may think that a particular ion has 2 hydrogens fewer or more depending on what she is looking for. However, a qualitative check can be performed on a single compound that is an unknown in order to determine whether, in its original form, it has a double bond or not. In this regard, a first run can be performed under protonation conditions, and a second run can be performed under deuteration conditions. The data from the two runs can be compared, and, if there is no mass shift with deuteration and protonation, then the unknown can be concluded to be an alkane ion having the form [M−H]+. If, instead, there is a double bond the ion will not hydride abstract and will show a mass shift.

While the foregoing has discussed the use of deuteration to explore compounds with similar class characteristics, such as alkanes, the GC-MS system 10 can also be used to perform hydrogen deuterium exchange (HDX) at atmospheric pressure. HDX can be utilized for determining additional structural information about individual analytes that may or may not define a single class of compounds but which share the common property of exchangeable hydrogens in their structure.

The GC-MS system 10 can be switched from a protonation/deuteration operating mode to an HDX mode by lowering the counter-current gas flow rate, lowering the extraction cone voltage, and lowering the sample cone voltage. To switch from protonation or deuteration to HDX the flow rate of the counter-current gas is reduced from about 25 liters/hour to about 40 liters/hour for protonation or deuteration to about 0 liters/hour for HDX; the extraction cone voltage is reduced from about 3 volts to about 6 volts for protonation or deuteration to about 1 volt to about 3 volts for HDX; and the sample cone voltage was reduced from 15 volts for protonation or deuteration to 10 volts for HDX. It is believed that the reaction occurs within the chamber 53 and that faster and higher energy conditions lead to deuteration and lower flows and lower energy conditions lead to HDX. To switch from protonation to HDX, the protonation reagent (e.g., H2O, MeOH-d0) in the source enclosure 30 must also be changed out for a deuterated reagent (e.g., D2O, MeOH-d3, MeOH-d4). The GC-MS system 10 can be switched between deuteration and HDX modes without a reagent change.

In some instances, a comparative study can be performed that includes a first GC-MS run under protonation (or deuteration without HDX) conditions and second GC-MS run under HDX conditions. The data acquired from the first and second runs can then be compared to see the changes. Such a comparative study could be used to examine the presence or absence, or relative amounts of additives in a sample. For example, such a comparative study could be utilized to determine the relative abundance of one additive versus another additive in the sample.

Another experiment that HDX can be used for is for unknown analysis. This is a comparative analysis that looks for distinctive mass shifts that might indicate the presence of something that was not expected to be present. Unknown analysis can also provide information about elemental composition with some number carbons, hydrogen, and nitrogens.

HDX can also be used in two other areas. It can be used to improve an ion mobility separation, or to affect a quantitative assay. For instance, with the mass shift associated with the exchange of deuterium for hydrogen, if one wanted to target an analyte that at low mass was interfered with, but had characteristic mass shift under HDX conditions, the mass could be shifted via HDX simply to do MS/MS on the result to prevent the interference. So the reaction can be performed not for the results of the reaction itself, but to enable background removal or improve ion mobility.

Additional gas phase reactions can be performed within the chamber 53 that may allow other selectivity or provide additional structural information about classes of analytes or individual compounds. One of these is the selective addition of halogens (e.g., chlorine) to aromatic analytes. In this approach, the addition of the halogen can be encouraged or discouraged based on source conditions so that the data suits the purpose of the assay. This approach appears to lead to selective addition of a halogen to aromatic compounds.

A vial containing chlorinated solvent (chloroform) is placed in the source enclosure 30 with the GC-MS system 10 being initially set to operate under protonation conditions (Table 1, above). To see the reaction products, the flow rate of the counter-current gas can be reduced to about 25 liters/hour, and the flow rate of the auxiliary gas can be lowered to about 0 liters/hour. To eliminate the reaction products the flow rate of the counter-current gas can be raised to about 40 liters/hour, and the flow rate of the auxiliary gas can be raised to about 400 liters/hour. This approach appears to be selective for aromatics. It also appears that the addition is not just chlorine but the addition of CCl or 47 Da to the molecular weight of the analyte.

In one example, a first GC-MS run can be performed under conditions in which the reaction products are eliminated. A second GC-MS run can be performed under conditions that produce the reaction products. The two runs can be performed in either order. Data from the two runs can then be compared. Aromatics will exhibit a characteristic mass shift when analyzed under conditions that produce the reaction products while other classes of compounds in the sample will not exhibit a mass shift when comparing the data. This characteristic mass shift can be used to keep the data corresponding to the aromatics and remove data corresponding to the other classes of compounds. In this regard, the collected data can be post-processed using a Strip function implemented in software to strip out the unwanted data.

The selective addition of halogens to aromatic analytes can also be used in two other areas. It can be used to improve an ion mobility separation, or to affect a quantitative assay. For instance, if one wanted to target an aromatic analyte that at low mass was interfered with, the mass could be shifted via the addition of the halogen simply to do MS/MS on the result to prevent the interference. So the reaction can be performed not for the results of the reaction itself, but to enable background removal or improve ion mobility.

In some cases, a catalyst may be provided in the chamber 53. This can be used to provide for chemical reaction without ionization. For example, a catalyst could be provided in the chamber to cause a change in a chemical reaction that would result in the lack of ionization of a compound or a class of compounds that otherwise would ionize in the absence of the catalyst. That is, the catalyst may cause condensation or precipitation or reaction in the chamber 53 that causes a certain compound or a certain class of compounds not to ionize, e.g., for adjusting selectivity.

In a differential experiment, for example, a sample can be run (in a GC-MS run) under a first set of conditions to see all the peaks, and it can be run again under a different set of conditions to see specific peaks of a certain class or substructure disappear or change while others remain unaffected. A catalyst is one prospect for doing this.

Alternatively or additionally, catalysis in the chamber may be utilized to extend the range of analytes by causing chemical conversion of compounds to more readily ionized species. Alternatively or additionally, a catalyst may be provided in the chamber 53 for the creating a mass shift to target analytes that are interfered with at low mass.

There are several ways that a catalyst may be introduced into the chamber 53. The catalyst can be introduced in liquid form. For example, a vial containing a liquid catalyst can be placed within the source enclosure 30, which, after heating and vaporizing, will enter the chamber 53 via the gap 61. Alternatively or additionally, a catalyst in solid/substrate form may be placed directly in the chamber and/or in or along the path of the effluent entering the chamber 53. For example, a catalyst in substrate form may be placed in the bottom of the chamber 53 for the gas phase effluent to react over.

The catalyst may be of the type typically applied in petrochemical applications or titanium dioxide.

Other implementations are within the scope of the following claims.

What is claimed is:

1. A gas chromatography-mass spectrometry (GC-MS) method comprising:
    performing a GC-MS run on a sample using a gas chromatography-mass spectrometry system to determine protonated GC-MS data for the sample; and
    performing a GC-MS run on the sample using the gas chromatography-mass spectrometry system to determine deuterated GC-MS data for the sample; and
    performing a strip function to generate processed GC-MS data comprising the deuterated GC-MS data with alkane data removed, the strip function operating to compare the protonated GC-MS data and the deuterated GC-MS data to determine the alkane data corresponding to one or more compounds in the sample that ionize by hydride abstraction by:
        identifying the alkane data corresponding to one or more analyte ions that do not exhibit a mass shift when ionized under deuteration conditions based on the protonated GC-MS data and the deuterated GC-MS data; and
        removing the alkane data corresponding to compounds that ionize by hydride abstraction from the deuterated GC-MS data.

2. The method of claim 1, the protonated GC-MS run performed using a reagent selected from the group consisting of $H_2O$ and MeOH-d0.

3. The method of claim 1, the deuterated GC-MS run performed using a reagent selected from the group consisting of $D_2O$, MeOH-d3, and MeOH-d4.

4. The method of claim 1, further comprising generating ions in the protonated GC-MS run and the deuterated GCMS run by passing an effluent through a chamber disposed with a source enclosure of an atmpospheric pressure ionization source, wherein the atmospheric pressure ionization source comprises:
    a chamber device disposed within the source enclosure and comprising at least one wall defining the chamber; and
    a corona discharge pin disposed within the source enclosure and extending into the chamber, and
    wherein passing the effluent through the atmospheric pressure ionization source comprises passing the effluent into the chamber and through a corona discharge provided by the corona pin.

5. The method of claim 1, wherein at least one of the protonation conditions or the deuteration conditions comprise:
    an extraction cone voltage of about 3 volts to about 6 volts;
    a carrier gas flow rate of about 0.5 milliliters/minute to about 10 milliliters / minute;
    a makeup gas flow rate of about 250 milliliters / minute to about 500 milliliters / minute; or
    an auxiliary gas flow rate of about 100 liters/hour to about 300 liters/hour.

6. The method of claim 5, wherein at least one of the protonation conditions or the deuteration conditions comprise a counter-current gas flow rate of about 0 liters/hour to about 50 liters/hour.

7. The method of claim 1, wherein a protonation reagent for the protonation conditions comprises $H_2O$ and a deuteration reagent for the deuteration conditions comprises $D_2O$.

8. The method of claim 1, wherein the deuterated GC-MS is performed on the sample under deuteration conditions without hydrogen-deuterium exchange (HDX).

9. The method of claim 1, comprising determining whether an unknown ion is one of an alkane ion having a form of [M−H]+ or an alkene having a form of [M+H]+ based on a comparison of the protonated GC-MS data and the deuterated GC-MS data.

10. The method of claim 9, wherein the unknown ion is determined as being an alkane if the unknown ion does not exhibit a mass shift when ionized under deuteration conditions based on the protonated GC-MS data and the deuterated GC-MS data.

11. The method of claim 10, wherein the unknown ion is determined as being an alkene if the unknown ion exhibits a mass shift when ionized under deuteration conditions based on the protonated GC-MS data and the deuterated GC-MS data.

* * * * *

UNITED STATES PATENT AND TRADEMARK OFFICE
CERTIFICATE OF CORRECTION

| | |
|---|---|
| PATENT NO. | : 10,386,333 B2 |
| APPLICATION NO. | : 14/376862 |
| DATED | : August 20, 2019 |
| INVENTOR(S) | : Douglas M. Stevens |

Page 1 of 1

It is certified that error appears in the above-identified patent and that said Letters Patent is hereby corrected as shown below:

On the Title Page

Item (73) Assignee -- Please replace "WATERS TECHNOLOGY CORPORATION" with "WATERS TECHNOLOGIES CORPORATION" --

Signed and Sealed this
Fifteenth Day of October, 2019

Andrei Iancu
*Director of the United States Patent and Trademark Office*